(12) United States Patent
Feucht et al.

(10) Patent No.: US 6,345,192 B1
(45) Date of Patent: Feb. 5, 2002

(54) ELECTRODE STRUCTURE FOR ELECTRIC CONTACTOR

(75) Inventors: Peter Feucht, Blaustein; Albert Harder, Dornstadt-Tomerdingen, both of (DE); Mark J. Hastings, Castro Valley; John Evans, Forest Ranch, both of CA (US)

(73) Assignee: Venturi Medical Systems, LLC, Castro Valley, CA (US)

( * ) Notice: Subject to any disclaimer, the term of this patent is extended or adjusted under 35 U.S.C. 154(b) by 0 days.

(21) Appl. No.: 09/386,597

(22) Filed: Aug. 31, 1999

Related U.S. Application Data

(60) Provisional application No. 60/099,373, filed on Sep. 8, 1998.

(51) Int. Cl.[7] .................................................. A61B 5/04
(52) U.S. Cl. ....................................................... 600/387
(58) Field of Search .......................... 600/387, 372–395; 607/152

(56) References Cited

U.S. PATENT DOCUMENTS

| 3,640,270 A | | 2/1972 | Hoffmann | 128/128 |
|---|---|---|---|---|
| 3,783,865 A | | 1/1974 | Ricketts | 128/128 |
| 4,248,243 A | | 2/1981 | Niess et al. | 128/696 |
| 4,556,065 A | * | 12/1985 | Hoffmann | 600/387 |
| 4,646,747 A | * | 3/1987 | Lundback | 600/387 |
| 4,736,749 A | * | 4/1988 | Lundback | 600/387 |
| 5,553,612 A | * | 9/1996 | Lundback | 600/387 |
| 5,722,404 A | * | 3/1998 | Lundback | 600/387 |
| 5,724,966 A | * | 3/1998 | Lundback | 600/387 |

FOREIGN PATENT DOCUMENTS

| DE | DT 25 48 805 | | 10/1975 | |
|---|---|---|---|---|
| DE | 2548805 | * | 5/1977 | 600/387 |
| EP | 0000759 | * | 8/1977 | 600/387 |
| EP | 0 000 759 | | 7/1978 | |

* cited by examiner

*Primary Examiner*—Linda C. M. Dvorak
*Assistant Examiner*—David M. Ruddy
(74) *Attorney, Agent, or Firm*—Fredrikson & Byron, P.A.

(57) ABSTRACT

A contactor for establishing electrical communication with organic tissue, the contactor including a cup-shaped housing of one-piece rubbery material including a closing end-wall connected across an annular sidewall with rim defining an open mouth into a main recess. An electrode in the recess comprises a contact plate with first side facing the mouth to contact organic tissue, and a second side with a pair of leg-like extensions and a center limiter post all of one-piece molded plastics coated with a thin layer of conductor preferably silver/silver chloride to be electrically conductive on the exterior surface of the electrode. The legs of the electrode snap fit against to physically and electrically connect with an electrically conductive venturi tube mounted extending through the housing, the venturi tube having a suction port positioned such that when high pressure gas is passed through the venturi tube, a vacuum is created within the housing recess.

7 Claims, 4 Drawing Sheets

ELECTRODE STRUCTURE FOR ELECTRIC CONTACTOR

A priority claim is hereby made to our pending U.S. Provisional application Serial No. 60/099,373 filed Sep. 8, 1998.

BACKGROUND OF THE INVENTION

1. Field of the Invention

The present invention is an improved contactor with improved electrode for diagnostic purposes, designed for establishing electric communication between organic tissue, such as the skin of a human or animal body, and circuitry of associated monitoring or testing instrument.

2. Brief Description of Prior Art

Prior art contactors related to the present invention are described in U.S. Pat. No. 3,640,270 issued Feb. 8, 1972 and U.S. Pat. No. 4,556,065 issued Dec. 3, 1985. Both patents name Heiner Hoffmann as the inventor. As disclosed in these prior patents, the typical prior art contactor of similar operation to the contactor of the present invention has a generally cup-shaped housing of non-metallic material with a mouth bounded by a tissue engaging rim; the housing contains an electrode which is recessed within the rim but accessible by way of its mouth so as to be able to make contact with the skin of a human or animal to be tested. The mouth of the cup communicates with a low air pressure zone or vacuum inside a conduit which is traversed by a flow of high-pressure gas, generally air, and is embedded in the elastomeric material of the housing. The low-pressure zone in the recess of the housing is used to secure the contactor against organic tissue. The venturi metal tube also forms part of a conductive connection between the external conduit and the electrode. The contact electrode of U.S. Pat. No. 4,556,065 use a relatively expensive plate of coherent particles-sintered or simply pressed of a mixture of silver and one or more silver salts such as silver chloride, silver bromide, silver rhodanide or silver cyanide. Such an electrode, which has low electrical contact resistance, must be protected from interaction with adjoining elements of different metallic materials which can give rise to detrimental local currents. It is for this reason, as described in the U.S. patents referred to above, a contact plate consisting of afore described compacted mixture of a metallic silver and a silver salt is supported on a metallic body coated with silver at least in its area adjoining the plate. U.S. Pat. No. 4,556,065 also shows a retaining screw which holds the contact plate onto the supporting body and consists at least on an outer surface of nonconductive material; a titanium screw, with an oxide layer on its surface. An electrode of this prior art type, comprising a massive metallic supporting body made at least partly of silver, is very expensive compared to the electrode of the present invention. Reference may also be made to prior art U.S. Pat. No. 4,248,243, showing a contactor connected to a diagnostic apparatus such as an electrocardiograph.

SUMMARY OF THE INVENTION

Disclosed is an improved contactor and electrode for establishing electrically conductive communication with organic tissue, the contactor including a cup-shaped housing of one-piece rubbery material, the material impervious to air passage, the housing including a closing end-wall connected across an annular sidewall. The sidewall has a free terminal edge defining a rim which defines or bounds an open mouth into a main recess of the housing. The electrode or improved electrode for contacting organic tissue is positioned in the recess. The electrode comprises a contact plate with first side facing the housing mouth, and a second side with a pair of leg-like extensions and a limiter post centered between the legs, the legs and limiter post coextensive away from the back side of the contact plate. The electrode is an inexpensive and lightweight one-piece molded plastics base or substrate which is coated with a thin and thus inexpensive exterior layer of silver/silver chloride so as to be electrically conductive on the exterior surface of the electrode. A coating of low resistance electrically conductive material such as a silver based material other than silver/silver chloride could be used on the exterior of the electrode, although we prefer silver/silver chloride. The leg extensions of the electrode are resilient and spaced apart for receiving a venturi tube snapped or clamped against by the legs to physically and electrically connect with a venturi tube. The venturi tube is mounted extending through the housing. The venturi tube is electrically conductive at least on the exterior surface thereof, and preferably is gold plated so corrosion will not occur and the high electrical conductivity will remain over a long period of time, although some other highly conductive non-corroding material might be used instead of the gold. The inexpensive electrode can be readily replaced, if ever needed due to wear with only the human hand (no tools). The electrode snaps in and out of place relative to the venturi and housing by hand. The electrode, venturi tube and housing are quite durable and can be chemically cleaned or sanitized, therefore our contactor is very inexpensive to use, such as in a hospital setting for a long period of time, such as years for example.

The venturi tube has a suction port positioned such that when high pressure gas (gas can herein be the same as air) is passed through the venturi tube, a low pressure or vacuum is created within the recess of the housing. Such vacuum in the recess is capable of allowing tissue, the tissue sealingly engaging the housing rim, and the housing to move toward one another to bring the tissue into contact with the electrode plate to establish electrical conductive contact with the tissue. The vacuum also holds the contactor stationary against the tissue regardless of orientation of the contactor, with this good holding power (improved over the prior art) aided by the fact the contactor is light in weight. The venturi tube is electrically conductive from the electrode legs to a threaded end of the tube, the threaded end is exposed for connection to a pressurized gas line which also includes an electrical conductor leading back to the testing instrument. The conductor of the gas line is connected to a conductive threaded end of the gas line which connects to the venturi tube, and the other end of the gas line conductor connects to or is part of a circuit of an associated testing or monitoring instrument. Whereby the patient tissue is electrically connected through the electrode plate to the electrode legs to the venturi tube to the threaded ends (or equivalent connectable ends) of the tube and gas supply line and the supply line output conductor (wire) to the associated testing or monitoring instrument such as an electrocardiograph for example.

The general object of our present invention is to provide an improved electrode structure useful for defining an improved contactor, and which is far less expensive, lighter in weight and thus more stable on tissue at a given vacuum, highly sensitive, and safer than those of the prior art, and capable of being disassembled and assembled such as for cleaning in a hospital setting without requiring tools beyond the human hands. Our contactor also retains and enhances the advantages of low contact resistance and avoidance of local voltage differences which can give rise to destructive currents. Another object is to provide structuring in the contactor for conveniently connecting our improved electrode to an external circuit of an associated instrument with the aid of a metallic venturi tube.

Our novel contactor with novel electrode is inexpensive to produce, provides improved functionality compared to the related prior art, and thus advances the art.

These, as well as other objects and advantages will become increasingly appreciated with continued reading and with an examination of the attached drawings.

DESCRIPTION OF THE PREFERRED EMBODIMENT

Figure 2:
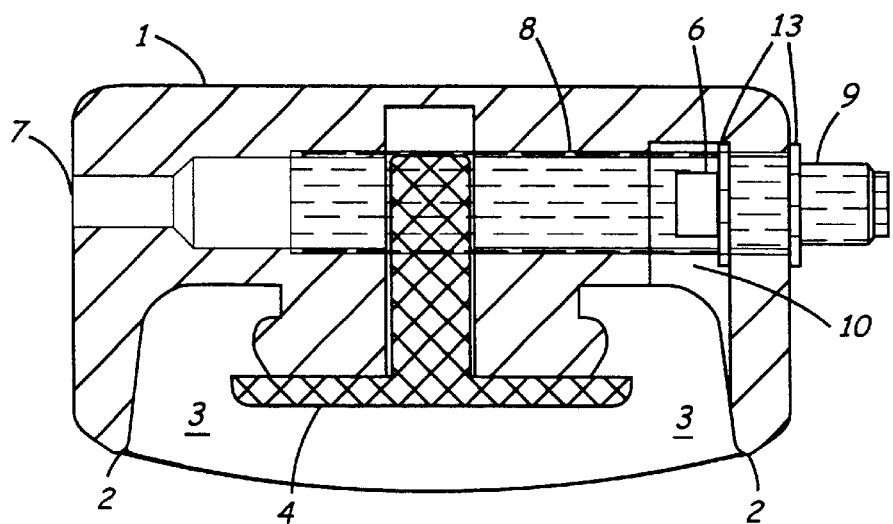
FIG. 2 is a cross sectional view of the assembled contactor of FIG. 1 and rotated 90 degrees.

Now with general reference to the drawings, our improved contactor 00 with improved electrode 18 includes a cup-shaped housing 1 of one-piece rubbery material, the material such as silicone rubber being impervious to air passage, the housing 1 including a closing end-wall 14 connected across an annular sidewall 15. The sidewall 15 has a free terminal edge defining a rim 2 which defines or bounds an open mouth 3 into a main recess 16 of the housing 1. In use, due to low pressure or vacuum, organic tissue 17 bows through mouth 3 to enter recess 16 and engages contact plate 4 of electrode 18, see FIG. 2. Rim 2 is for engaging tissue and creating a seal thereagainst, the sealing more easily accomplished due to the rubbery or flexible nature of housing 1 or rim 2. Within housing 1 is a central material extension 19 depending from the underside of closing end-wall 14 and defining a leg well 20 exposing therein a portion of the venturi tube 8 for the legs of the electrode to snap onto or clamp about, as can be ascertained from FIG. 2. The rubbery housing material defining the leg well 20 is sized relative to legs 5 to engage the electrode legs 5 on multiple sides, i.e., the outside surfaces and the two oppositely disposed left and right surfaces thereof and to thereby aid in holding the electrode 18 in proper place. The material defining leg well 20 also serves as a leg 5 guide when the electrode legs 5 are being inserted, initially or later in servicing, into the well and pushed toward venturi tube 8, the walls in well 20 accurately guide the legs 5 and prevent axial rotation relative to venturi tube 8 and thereby render it very easy to align and snap electrode legs 5 on the venturi tube 8.

Housing 1 includes a transverse through passage 21 in which venturi tube 8 resides. Generally passage 21 is smaller in diameter than the exterior of venturi tube 8 and thereby the material defining the passage 21 grips and frictionally holds venturi tube 8 in place after it has been forced into the passage 21. The tight fitting rubbery material of housing 1 also seals in the appropriate areas against venturi tube 8 and at the output end of venturi tube 8 forms the output passage beyond the end of venturi tube 8 for exhausting gasses from the contactor. Through passage 21 is defined or bounded by the rubbery material of housing 1, and therefore in addition to the previously mentioned through passage 21 opening into leg well 20, housing 1 includes an opening 10 to through passage 21 aligned or alignable with the suction port 6 of venturi tube 8 so vacuum can be created in the main recess of housing 1; an output port 7 in through passage 21 aligned with the gas output end of venturi tube 8 allowing the pressurized gas applied thereto to exhaust to the exterior of housing 1; and further includes an opening 22 in through passage 21 for the existing of the end 9 (threaded end) of venturi tube 8 to be exposed for connecting to a pressurized gas supply line 23 and an output electrical wire 24. Housing 1 can be made of silicone rubber although other rubbery or elastomeric materials which are also electrical insulators could be used to define housing 1.

Figure 1:
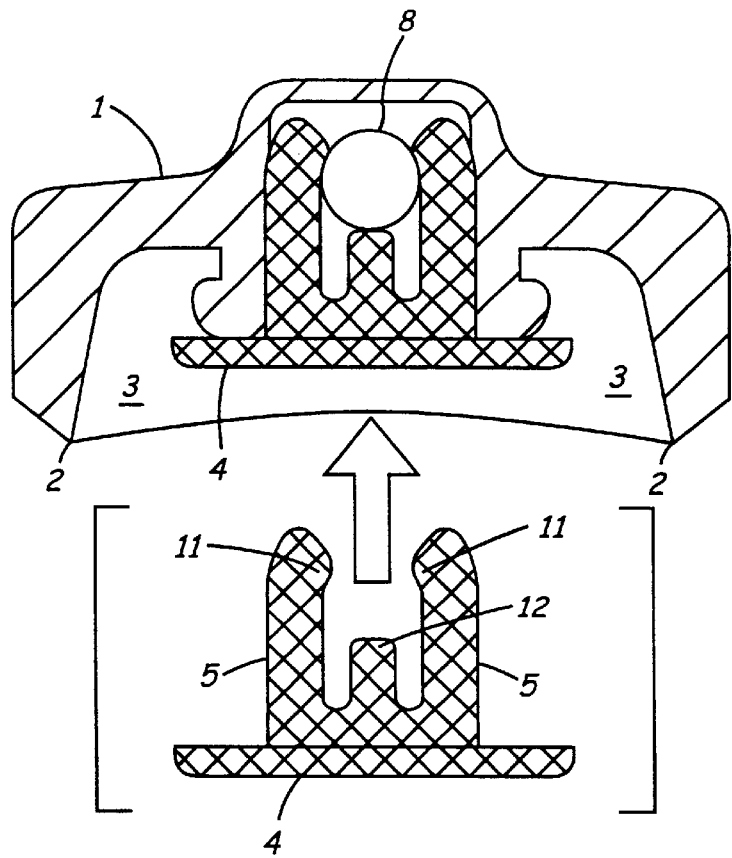
FIG. 1 is a cross sectional view of a contactor with electrode in accordance with the present invention. Shown is our new improved electrode structure in final operational position within the housing with the legs and limiter post within the leg well in the rubbery material of the closing end wall of the housing, and with the pronged legs snapped onto opposite sides of the venturi tube to clamp thereagainst, and the limiter post abutting the venturi tube. A portion of the housing end wall surrounding the leg well is shown firmly against the back side of the plate of the electrode and adding stability while aiding to prevent the electrode from moving too deeply into the recess of the housing. Also shown is the electrode structure in an unattached position with an arrow indicating direction of movement for snapping the electrode onto the venturi tube. The lower electrode is shown with a portion of the contact plate cut-away and showing plastics having a thin outer coating of silver/silver chloride.
Figure 3:
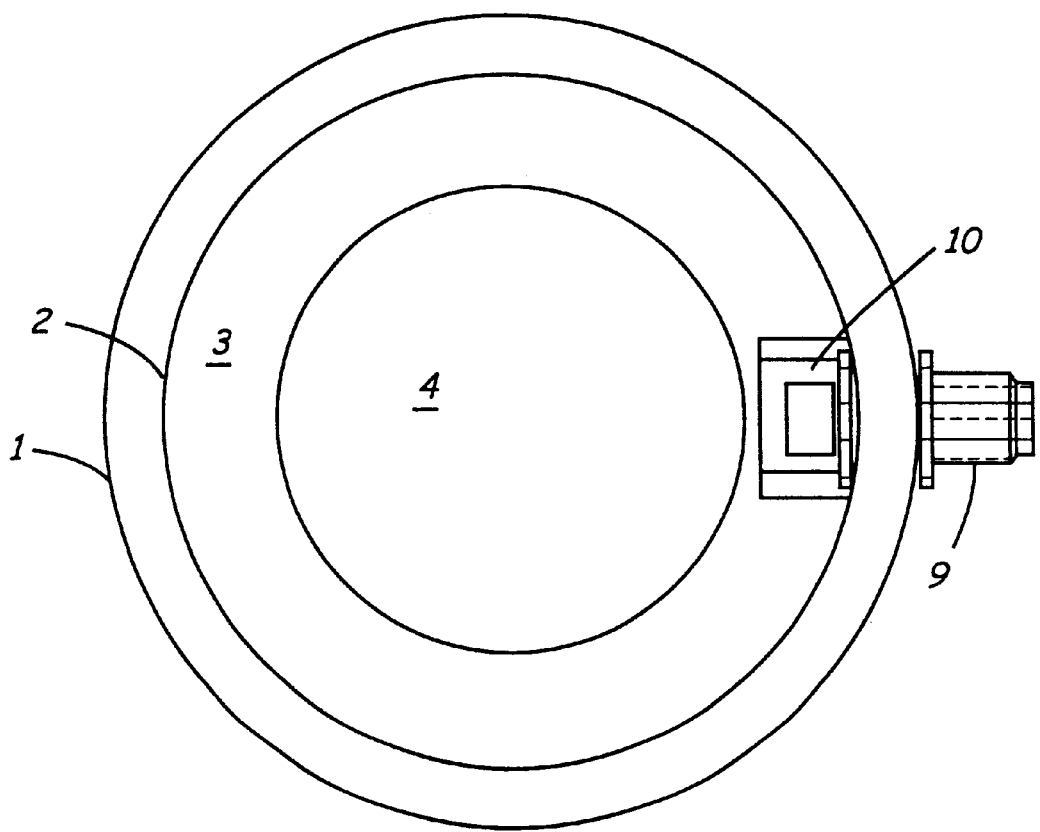
FIG. 3 is a bottom view of the FIG. 1 contactor and showing a plate of the electrode within the recess and at the mouth of the housing.

Our improved inexpensive, light-weight and snap-attach electrode 18 is positioned in housing 1 and at least in part exposed in recess 16 through mouth 3. Electrode 18 comprises a contact plate 4 with first side facing the housing mouth 3 and providing a surface for engaging organic tissue. The first side of electrode 18 is shown circular in FIG. 3, and is generally flat and smooth so as to not be abrasive to skin. For further comfort against the skin (tissue) the lower corner is a rounded-over or beveled corner 25 (see FIG. 1) so as to not be a sharp corner against the skin. An opposite and a second side of electrode contact plate 4 includes a pair of extensions or legs 5 and a limiter post 12 centered between the legs 5, the legs 5 and limiter post 12 coextensive away from the back side of the contact plate 4 and integrally molded of plastics therewith. The plastics 26 (see FIG. 1) from which electrode 18 is molded can be ABS, although other plastics could be utilized. Electrode 18 is a inexpensive one-piece molded plastics base or substrate, preferably injection molded low cost and accuracy of the part, which is coated with a thin and thus inexpensive exterior layer of silver/silver chloride 27 AgAgCl (again see FIG. 1) so as to be electrically conductive on the exterior surface of the electrode 18. Silver/silver chloride 27 in a thickness of 0.004 inches functions well, but the thickness can be varied widely within the scope of the invention. The layer or coating of silver/silver chloride 27 can be applied to the plastics substrate using any of numerous knows processes, one being to apply the silver/silver chloride into a liquid polymer, coat the plastics substrate therewith, and then set the polymer, such as with a catalyst for example. A coating of low resistance electrically conductive material such as a silver based material other than silver chloride or equivalent could be used on the exterior of the electrode within the scope of the invention although the silver/silver chloride provides a durable and resistance surfacing. The legs 5 of electrode 18 are resilient because of the plastics and shape thereof, and are spaced apart from one another for receiving venturi tube 8 in-between in a snap fit or clamping thereagainst to physically and electrically connect with venturi tube 8. The normal or non-loaded spacing between legs 5 in the area where tube 8 is clamped is less than the diameter or width of the venturi tube 8 so that the legs 5 are continuously trying to move inward when the tube 8 is clamped, as thereby clapping pressure and thus good contact is maintained between legs 5 and venturi tube 8. Each leg 5 includes what is in effect a curved indentation 11 in which the venturi tube 8 resides, the indention 11 as shown in FIG. 1 defined by the leg end curving inward to form hook or prong like structure overhanging the top of tube 8, thereby increase stability of the connection is provided, as well as increased surface area contact between legs 5 and venturi tube 8 for lower electrical resistant at the contact points. Limit or limiter post 12 extends up to contact the underside of venturi tube 8 and aid in supporting tube 8 and legs 5 properly positioned to one another. The terminal end of center material extension 19 of housing 1 abuts the back side of contact plate 4 and thereby provides further position stabilizing of the electrode 18 relative to venturi tube 8. Legs 5 fit snugly into leg well 20 and therefore rounded outer corners 28 as shown in FIG. 1 are applied to the distal outer ends of each leg 5 for prevent hanging-up or snagging of the legs against the housing material defining well 20 when legs 5 are pushed into the well 20 to engage venturi tube 8. Starter slopes or ramps 33 are provided on the inside distal ends of both the legs 5 to serve as spread-directing ramps which with initial engagement against the sidewall of venturi tube 8 during the electrode snapping-in process, the legs spread out to allow the passage of a portion of the distal legs ends beyond at least the widest portion of tube 8 followed by resilient returning against tube 8.

Figure 5:
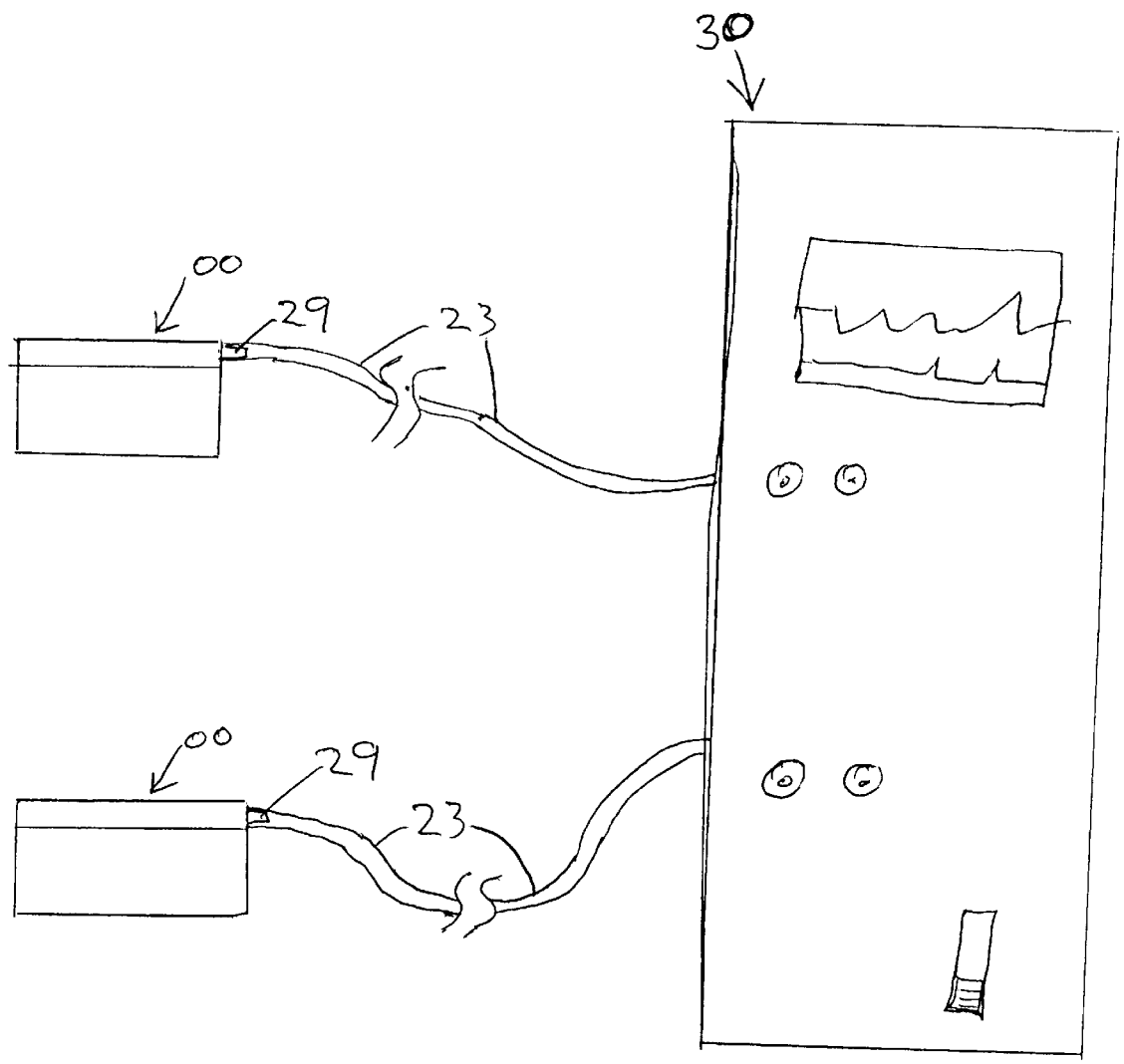
FIG. 5 is an illustration indicating two contactors in accordance with the invention and connected to a monitoring or testing instrument which also includes pressured gas supply to the gas lines to the contactors.

Venturi tube 8 is an elongate tube of brass, copper or steel, which is electrically conductive at least on the exterior surface thereof, and preferably is gold plated so corrosion will not occur and the high or higher electrical conductivity provided by the plating over the base or substrate material (brass) will remain over a long period of time. Venturi tube 8 has an internal venturi arrangement with a suction port 6 positioned such that when fast moving or high pressure gas (gas can herein be the same as air) is passed through the venturi tube 8, a low pressure or vacuum is created by the venturi and is communicated with the recess 16 of the housing 1. Such vacuum in the recess 16 is capable of allowing tissue 17, the tissue sealingly engaging the housing 1 rim 2, and the housing 1 to move toward one another to bring the tissue 17 into contact with the electrode plate 4 to establish electrical conductive contact with the tissue. The vacuum also holds the contactor 00 stationary against the tissue regardless of orientation, i.e., vertical, up-side-down, with this good holding power (improved over the prior art) aided by the fact the contactor 00 is light in weight. The venturi tube 8 is electrically conductive from the electrode legs 5 to a threaded end 9 of the tube 8, the threaded end 9 is exposed for connection to a pressurized gas line 23 which also includes an output electrical conductor 24. The conductor 24 of the gas line 23 is connected to a conductive threaded end 29 of the gas line 23 which connects at end 9 to the venturi tube 8, and the other end of the gas line conductor 24 (wire) connects to or is part of a circuit of an associated testing or monitoring instrument 30 shown in drawing FIG. 5. Whereby the patient tissue 17 is electrically connected through the electrode plate 4 to the electrode legs 5 to the venturi tube 8 to the threaded ends 9, 29 (or equivalent connectable ends) of the tube 8 and gas supply line 23 and the supply line conductor 24 to the associated testing or monitoring instrument such as an electrocardiograph for example. Venturi tube 8 fits tightly into passage 21 of housing 1, and includes one or more collars 13 shown in FIG. 2 to aid in stabilizing and sealing the tube relative to the housing.

Figure 4:
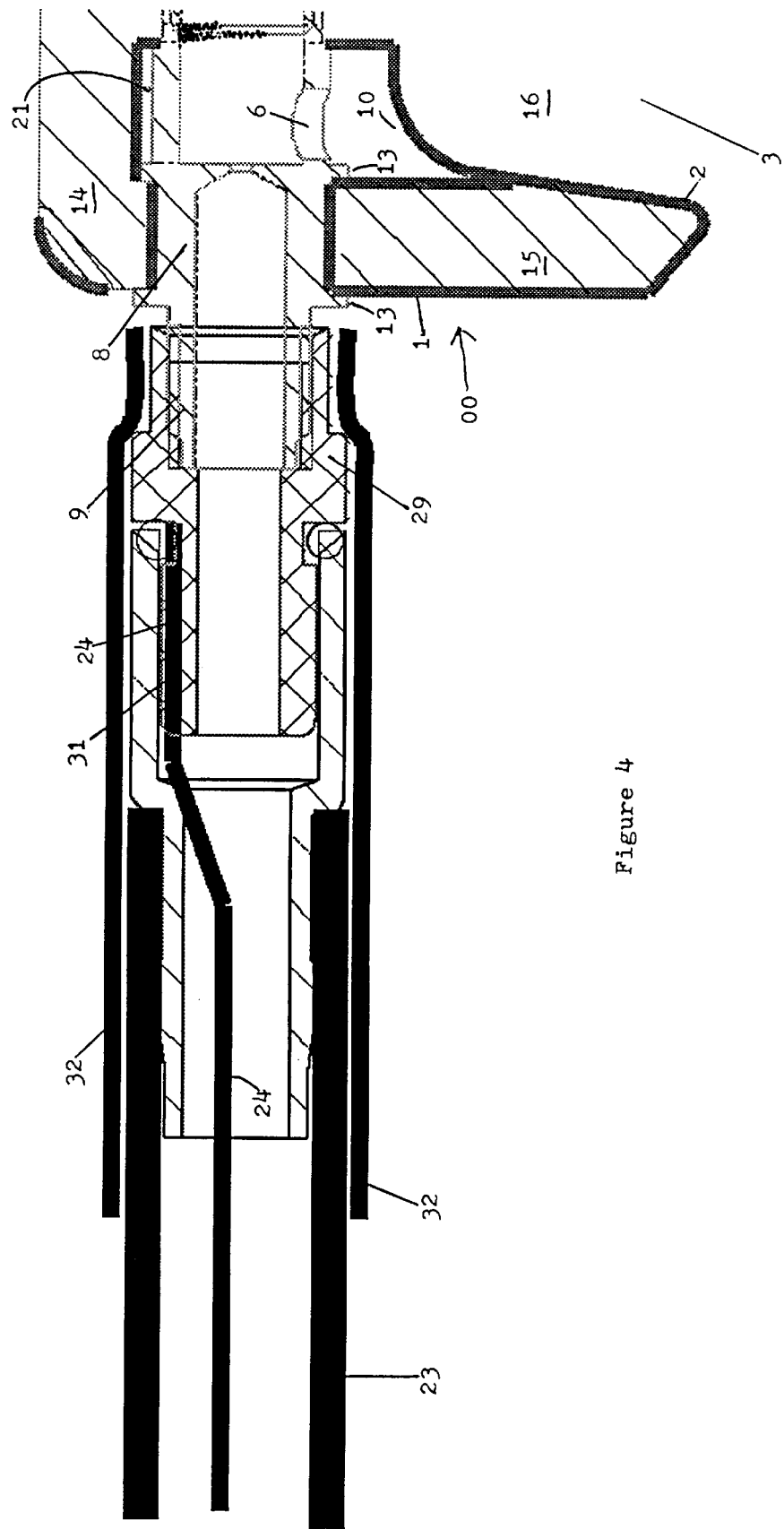
FIG. 4 is a cross sectional view of a portion of the contactor for illustrating a pressurized gas supply line and electrical conductor connected to an exposed end of the venturi tube.

FIG. 4 is a cross sectional view of a portion of the contactor for illustrating a pressurized gas supply line and electrical conductor connected to an exposed end of the venturi tube. Shown is a corner edge of contactor 00 with housing 1 having rim 2, mouth 3, recess 16, end plate 14, through passage 28 with venturi tube 8 therein, flanges 13 suction opening 6 and threaded end 9. Also shown is gas supply line 23 connected to threaded end 29 threadably engaged with end 9, electric wire 24 within line 23 and connected to threaded end 29 by being sandwiched or compressed at 31 between two metal or conductive parts of 29, the exterior of threaded end 29 and adjacent connected end of line 23 are covered with a layer of insulating tubing 32 such as heat shrinkable tubing.

We have found that the described reusable contactor 00 can, detect bioelectric contact potentials of low magnitude on human or animal tissue which can be transmitted to a variety of diagnostic devices.

While we have described our invention in great detail, the details are not to be used to unreasonably restrict the true scope of the invention as determined by broad and reasonable interpretation of the herewith included claims.

We claim:

1. A contactor for establishing electric communication with organic tissue comprising:
    a cup shaped housing, said housing of rubbery material with a mouth bounded by a rim, the rim for engaging organic tissue, said mouth opening into a main recess of said housing;
    an electrode within said housing, said electrode comprising a contact plate having a first side within said recess toward said mouth and recessed below said rim, and a second side with integrally connected resilient legs, said electrode contact plate and legs of one-piece molded plastics and coated with an outer layer of silver/silver chloride so as to have an electrically conductive exterior surface; said resilient legs residing within a leg well of said housing and clamping against
    a venturi tube having means for creating a suction at a suction port thereof upon passage of pressurized gas through said venturi tube, said venturi tube arranged with the suction port thereof positioned in communication with the main recess of said housing, whereby suction at the suction port can create low pressure in the housing recess, said venturi tube mounted to said housing with an end of the venturi tube positioned for allowing connection of the venturi tube end to a pressurized gas supply line and an output electrical wire, said venturi tube including gold plating so as to be electrically conductive from at least the engagement of said resilient legs of said electrode to the exposed end of the venturi tube so as to serve as an electrical conductor between said electrode and an output electrical wire when the wire is electrically connected to the venturi tube end.

2. A contactor for establishing electric communication with organic tissue according to claim 1 wherein said resilient legs are a pair of spaced apart legs, each of the legs includes a curved indentation, and the legs are snap-attached to said venturi tube with the venturi tube positioned between the pair of legs and residing in the curved indentations, and further including a movement limiting post connected to said second side of said contact plate and extending therefrom and abutting against said venturi tube, whereby said limiting post aids in holding said venturi tube positioned and in contact with the resilient legs.

3. A contactor for establishing electric communication with organic tissue comprising:

a housing, said housing including a mouth bounded by a rim of rubbery material, the rim for engaging organic tissue, said mouth opening into a main recess of said housing;

an electrode within said housing, said electrode comprising a contact plate having a first side within said recess toward said mouth, and a second side with integrally connected extending members, the electrode contact plate and extending members of one-piece molded plastics and coated with an outer layer of electrically conductive silver containing material; said extending members engaging against a venturi tube having means for creating a suction at a suction port thereof upon passage of pressurized gas through said venturi tube, said venturi tube arranged with the suction port thereof positioned in communication with the main recess of said housing, whereby suction at the suction port can create low pressure in the housing recess, said venturi tube mounted to said housing with an end of the venturi tube positioned for allowing connection of the venturi tube end to a pressurized gas supply line and an output electrical wire, said venturi tube electrically conductive from at least the engagement of said extending members of said electrode to the exposed end of the venturi tube so as to serve as an electrical conductor between said electrode and an output electrical wire when connected to the venturi tube end.

4. A contactor for establishing electric communication with organic tissue according to claim 3 wherein said venturi tube is gold plated for providing a non-corroding exterior conductive surface.

5. A contactor for establishing electric communication with organic tissue according to claim 4 wherein said outer layer of electrically conductive silver containing material is primarily silver/silver chloride.

6. A contactor for establishing electric communication with organic tissue according to claim 5 wherein said housing is of silicone rubber.

7. A contactor for establishing electric communication with organic tissue comprising:

a housing defining a mouth opening into a main recess of said housing; an electrode at least in part exposed within the main recess of the housing, said electrode comprising a conductive contact plate within said recess toward said mouth, said electrode further including resilient holding means for electrically connectively engaging a venturi tube in an electrically conductive area of said venturi tube;

said venturi tube having means for creating a suction at a suction port venturi tube arranged with the suction port thereof positioned in communication with the main recess of said housing, said venturi tube including means for allowing connection of the venturi tube to a pressurized gas supply line and an output electrical wire;

wherein said resilient holding means includes a pair of legs of resilient material in spaced relationship with one another and sized, shaped and positioned to snap onto said venturi tube wherein the venturi tube is clamped between the pair of legs, and further wherein a movement limiting post abuts against said venturi tube between the pair of legs.

\* \* \* \* \*